United States Patent
Ringlien

(10) Patent No.: US 7,148,961 B1
(45) Date of Patent: Dec. 12, 2006

(54) CONTAINER SIDEWALL INSPECTION

(75) Inventor: James A. Ringlien, Maumee, OH (US)

(73) Assignee: Owens-Brockway Glass Container Inc., Perrysburg, OH (US)

(*) Notice: Subject to any disclaimer, the term of this patent is extended or adjusted under 35 U.S.C. 154(b) by 195 days.

(21) Appl. No.: 10/988,031

(22) Filed: Nov. 10, 2004

(51) Int. Cl.
*G01N 21/88* (2006.01)
*G01N 21/90* (2006.01)

(52) U.S. Cl. .............................. 356/240.1; 356/239.1; 250/223 B

(58) Field of Classification Search .. 356/239.1–240.1, 356/428–430; 250/223 B
See application file for complete search history.

(56) References Cited

U.S. PATENT DOCUMENTS

| | | | |
|---|---|---|---|
| 3,030,516 A | 4/1962 | Seavey | |
| 3,758,215 A | 9/1973 | Paruolo et al. | |
| 3,932,042 A | 1/1976 | Faani et al. | |
| 4,025,201 A | 5/1977 | Deane | |
| 4,378,493 A | 3/1983 | Dorf et al. | |
| 4,500,203 A | 2/1985 | Bieringer | |
| 4,547,067 A | 10/1985 | Watanabe | |
| 4,579,227 A | 4/1986 | Miller | |
| 4,584,469 A | 4/1986 | Lovalenti | |
| 4,601,395 A | 7/1986 | Juvinall et al. | |
| 4,610,542 A | 9/1986 | Ringlien | |
| 4,655,349 A | 4/1987 | Joseph et al. | |
| 4,664,521 A | 5/1987 | Scott et al. | |
| 4,664,525 A | 5/1987 | Tagaya | |
| 4,691,231 A | 9/1987 | Fitzmorris et al. | |
| 4,750,035 A | 6/1988 | Chang et al. | |
| 4,915,237 A | 4/1990 | Chang et al. | |
| 4,967,070 A * | 10/1990 | Ringlien et al. | ........ 250/223 B |
| 4,983,822 A | 1/1991 | Fukuchi | |
| 5,233,186 A | 8/1993 | Ringlien | |
| 5,243,400 A | 9/1993 | Ringlien | |
| 5,442,446 A | 8/1995 | Gerber et al. | |
| 5,486,692 A | 1/1996 | Baldwin | |
| 5,895,911 A | 4/1999 | Giometti et al. | |
| 5,898,169 A | 4/1999 | Nordbryhn | |
| 6,067,155 A | 5/2000 | Ringlien | |
| 6,133,999 A | 10/2000 | Myers et al. | |
| 6,369,889 B1 | 4/2002 | Olschewski | |
| 6,424,414 B1 | 7/2002 | Weiland et al. | |
| 6,618,495 B1 | 9/2003 | Furnas | |
| 6,795,176 B1 * | 9/2004 | Tennakoon et al. | ...... 356/239.1 |
| 7,060,999 B1 * | 6/2006 | Juvinall | ................. 250/559.44 |
| 2001/0054680 A1 | 12/2001 | Lindner | |

FOREIGN PATENT DOCUMENTS

JP   353021975 A   2/1978

(Continued)

*Primary Examiner*—Hoa Q. Pham

(57) ABSTRACT

Apparatus for inspecting containers having a sidewall with a shoulder and a heel includes a device for positioning a container for inspection, a light source on one side of the container positioning device, and a camera having a light sensor and an entrance pupil on an opposing side of the container positioning device. A fresnel lens is disposed between the camera and the positioning device. The fresnel lens is positioned with respect to the entrance pupil of the camera so that the light sensor has a field of view that is directed by the fresnel lens through the container sidewall onto the light source at a first converging angle through the shoulder and at a second converging angle through the heel. The positioning device preferably is such that the front surface of the container is positioned adjacent to the fresnel lens, and such that the fresnel lens has a focal point disposed between the front surface and the light source.

11 Claims, 1 Drawing Sheet

| | FOREIGN PATENT DOCUMENTS | | | JP | 358099738 A | 6/1983 |
|---|---|---|---|---|---|---|
| | | | | JP | 358184537 A | 10/1983 |
| JP | 353021976 A | 2/1978 | | JP | 402114158 A | 4/1990 |
| JP | 355027913 A | 2/1980 | | | | |
| JP | 355104744 A | 8/1980 | | * cited by examiner | | |

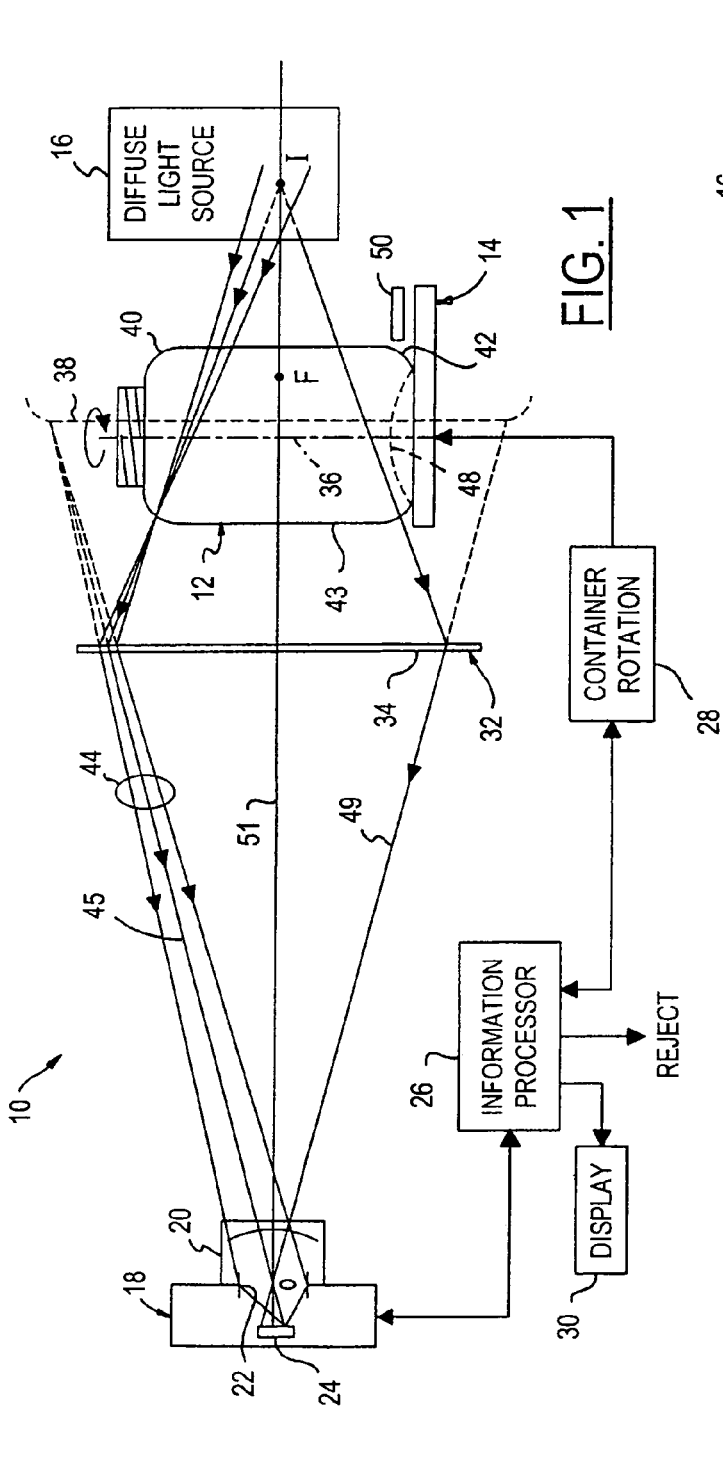
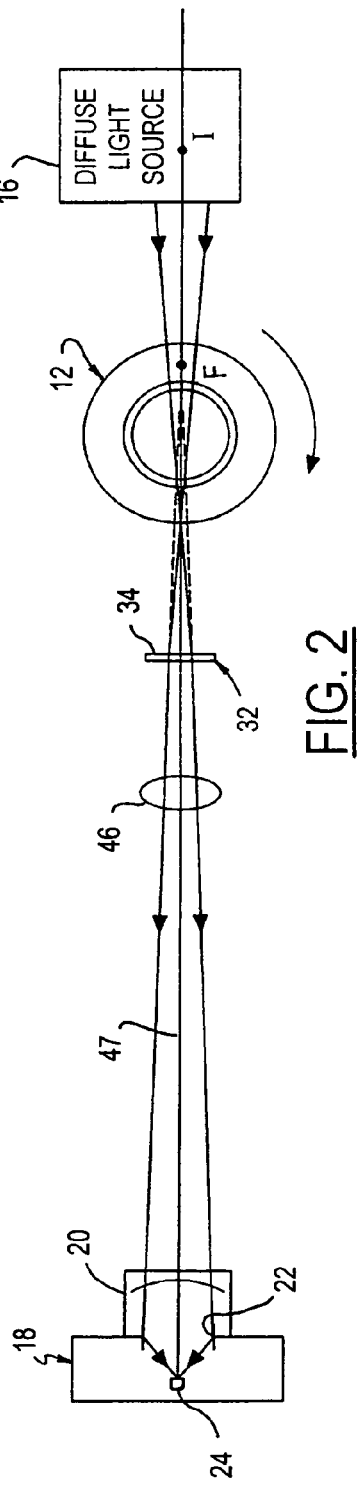

CONTAINER SIDEWALL INSPECTION

The present invention is directed to inspection of container sidewalls for commercial variations that affect the optical properties of the containers.

BACKGROUND AND SUMMARY OF THE INVENTION

In the manufacture of containers such as glass bottles and jars, various types of anomalies can occur in the sidewalls, heels, bottoms, shoulders, necks and/or finishes of the containers. These anomalies, termed "commercial variations" in the art, can affect commercial acceptability of the containers. It has been proposed to employ electro-optical inspection techniques for detecting commercial variations that affect the optical properties of the containers. The basic principle is that a light source is positioned to direct light energy onto the container, and a light sensor is positioned to receive an image of a portion of the container illuminated by the light source. U.S. Pat. Nos. 4,378,493, 4,610,542, 5,442,446 and 6,067,155 disclose inspection systems in which a light source and a light sensor are positioned on opposite sides of a container under inspection. Opaque and refractive commercial variations, in a portion of the container illuminated by the light source, are detected as a function of light intensity in an image of the illuminated portion of the container received at the sensor.

A problem is encountered when inspecting the sidewalls of containers, particularly large-diameter containers such as baby food jars and other food containers. The push-up on the container base, the curvature of the container shoulder and/or heel, and the container support mechanism on the back side of the container can affect the ability to inspect the entire container sidewall and result in false indications of commercial variations in the container sidewall. Inspection systems consequently typically inspect the central portion of the container sidewall, and leave the shoulder and heel portions uninspected. It is a general object of the present invention to provide an apparatus for inspecting container sidewalls in which the shoulder and/or heel portion of the container sidewall can be inspected without producing false indications of commercial variations.

Apparatus for inspecting containers having a container sidewall with a shoulder and a heel, in accordance with one aspect of a presently preferred embodiment of the invention, includes a device for positioning a container for inspection, a light source on one side of the container positioning device, and a camera having a light sensor and an entrance pupil on an opposing side of the container positioning device. A lens, preferably a fresnel lens, is disposed between the camera and the positioning device. The fresnel lens is positioned with respect to the entrance pupil of the camera so that the light sensor has a field of view that is directed by the fresnel lens through the container sidewall onto the light source at a first converging angle through the shoulder and at a second converging angle through the heel. The positioning device preferably is such that a front surface of the container is positioned adjacent to the fresnel lens, and such that the fresnel lens has a focal point disposed between the container front surface and the light source. The container positioning device may take any number of forms, but preferably is such as to hold the container in stationary position while rotating the container around an axis. The focal point of the fresnel lens preferably is disposed between the light source and the axis of container rotation.

Apparatus for inspecting a container sidewall having a shoulder and a heel, in accordance with a second aspect of the preferred embodiment of the invention, includes a device for positioning a container for inspection, a light source on one side of the container positioning device, and a camera having a light sensor with a field of view and an entrance pupil on an opposing side of the positioning device from the light source. A lens system is disposed between the camera and the positioning device such that an upper portion of the camera field of view is directed by the lens system, preferably a fresnel lens, at a downward angle through the container shoulder toward the light source, and a lower portion of the camera field of view is directed by the lens system at an upward angle through the container heel toward the light source. The lens system preferably directs the rays of the camera's line of sight through a field of view at the container wall being inspected to a convergence point at or near the light source.

BRIEF DESCRIPTION OF THE DRAWINGS

The invention, together with additional objects, features, advantages and aspects thereof, will best be understood from the following description, the appended claims and the accompanying drawings, in which:

FIG. 1 is an electro-optical schematic diagram that illustrates an apparatus in side elevation for inspecting container sidewalls in accordance with one presently preferred embodiment of the invention; and FIG. 2 is a schematic top plan view of the apparatus illustrated in FIG. 1.

DETAILED DESCRIPTION OF PREFERRED EMBODIMENTS

The drawings illustrate an apparatus 10 for inspecting the sidewall of a container 12 in accordance with one presently preferred embodiment of the invention. Container 12 is positioned for inspection by a positioning device or apparatus 14. This positioning device preferably comprises a conveyor of the type illustrated in U.S. Pat. No. 4,378,493 or 6,581,751 for bringing successive containers into position for inspection, and holding the containers in stationary position while rotating the container around its axis. As a less preferred alternative, the positioning device 14 may comprise a linear conveyor that conveys successive containers through the inspection station.

A diffuse light source 16 is positioned on one side of container positioning device 14, and a camera 18 is positioned on the opposing side of positioning device 14. Camera 18 preferably includes a lens system 20 for focusing light energy through an entrance pupil 22 onto a light sensor 24. Light sensor 24 preferably takes the form of a linear array CCD sensor having a long dimension parallel to the axis of container 12 at the inspection position. Sensor 24 is connected to an information processor 26 for scanning the sensor at periodic intervals. Information processor 26 preferably also is connected to a container rotation device 28, such as a drive roller, for controlling rotation of container 12 so that information processor 26 can scan sensor 24 at increments of container rotation. Such increments of container rotation may be equal angular increments of container rotation, or equal time increments while the container is rotated at constant angular velocity. Information processor 26 also is connected to a suitable device 30 for displaying the results of the container inspection process, and to a suitable device for rejecting containers that do not pass the inspection process.

A lens system 32 is positioned between sensor 24 and container positioning device 14 for controlling the field of view of the sensor relative to container 12 in device 14. Lens system 32 preferably comprises a fresnel lens 34 having a focal point F positioned between light source 16 and the axis 36 of container rotation. Lens 34 has an object point O at camera entrance pupil 22, and a convergence point I at or near diffuse light source 16. The relationship among the distances from lens 34 to points F, O and I is defined by the classic lens equation $1/F=1/O+1/I$. Inasmuch as the front surface of container 12 (i.e., the container surface facing camera 18) is placed at less than the fresnel lens focal length from the fresnel lens, camera 18 "sees" a magnified virtual image 38 of the front sidewall and is focused on this magnified virtual image.

As shown in FIG. 1, fresnel lens 34 functions to direct an upper portion of the camera field of view at a downward converging angle through the container shoulder 40, and to direct a lower portion of the camera field of view at an upward converging angle through the container heel 42. (Directional words such as "upward" and "downward" are employed by way of description and not limitation with respect to the upright orientation of container 12 illustrated in FIG. 1.) The light sensor field of view thus is directed not only through the cylindrical portion 43 of the container sidewall, but also through the container shoulder and heel to the convergence point I at light source 16. FIG. 1 illustrates a cone 44 of rays from light source 16 through container shoulder 40 and lens 34 that are focused by lens 34 through entrance pupil 22. Cone 44 is shown surrounding a chief ray 45, which passes through the center of pupil 22. (The term "chief ray" is employed in its usual sense to refer to a ray directed toward the center of the camera entrance pupil. The term "cone of rays" refers to the rays surrounding the chief ray that are at angles that will permit passage through the entrance pupil of the camera.) At the lower end of the camera field of view, only chief ray 49 is shown for clarity. A center chief ray 51 lies along the optical axis of sensor 24. Likewise, FIG. 2 illustrates a cone of rays 46 and a chief ray 47 from light source 16 through container 12 that are focused by lens 34 through camera entrance pupil 22. The size of entrance pupil 22 is exaggerated in FIGS. 1 and 2 to show shallow angle crossovers of the rays at the container.

Positioning of fresnel lens 34 between camera 18 and container 12 yields three advantages: (1) the camera views a larger area of the container sidewall, including shoulder 40 and heel 42; (2) the camera "sees" a magnified virtual image of 38 of the container sidewall; and (3) the camera "uses" only a small area of light source 16 through the fresnel lens and the container, so the physical size of the light source can be greatly reduced. It also will be noted in FIG. 1 that the lower portion of the camera field of view does not intersect the push-up 48 at the container bottom, and does not intersect or "see" the support element 50 of positioning device 14. (Support element 50 may be a back-up rail in above-noted U.S. Pat. No. 4,378,493 or a back-up roller in above-noted U.S. Pat. No. 6,581,751.) Thus, the push-up and support element do not result in erroneous indications of commercial variations at sensor 24 and information processor 26, or exclude regions of the container from inspection.

There thus have been disclosed an apparatus and method for inspecting a container sidewall that fully achieves all of the objects and aims set forth above. The invention has been disclosed in conjunction with a presently preferred embodiment thereof, and a number of modifications and variations have been discussed. Other modifications and variations readily will suggest themselves to persons of ordinary skill in the art in view of the foregoing discussion. The invention is intended to embrace all such modifications and variations as fall within the spirit and broad scope of the appended claims.

The invention claimed is:

1. Apparatus for inspecting containers having a sidewall that includes a shoulder and a heel, which includes:

a device for positioning a container for inspection, a light source on one side of said container positioning device, a camera having a light sensor and an entrance pupil on an opposing side of said positioning device from said light source, and a fresnel lens disposed between said camera and said positioning device, said fresnel lens being positioned with respect to said entrance pupil such that said sensor has a field of view that is directed by said fresnel lens through said sidewall at a first converging angle through the shoulder onto said light source and at a second converging angle through the heel onto said light source.

2. The apparatus set forth in claim 1 wherein said positioning device is such that a front surface of the container is positioned adjacent to said fresnel lens, and such that said fresnel lens has a focal point disposed between said front surface and said light source.

3. The apparatus set forth in claim 1 wherein said container positioning device include means for rotating the container around an axis.

4. The apparatus set forth in claim 3 wherein said positioning device is such that a front surface of the container is positioned adjacent to said fresnel lens, and such that said fresnel lens has a focal point disposed between said front surface and said light source.

5. The apparatus set forth in claim 4 wherein said focal point is disposed between said axis and said light source.

6. The apparatus set forth in claim 5 wherein said light source is a diffuse light source.

7. Apparatus for inspecting a container sidewall having a shoulder and heel, which includes:

a device for positioning a container for inspection, a diffuse light source on one side of said container positioning device, a camera having a light sensor with a field of view and an entrance pupil on an opposing side of said positioning device from said light source, and a lens system disposed between said camera and said positioning device such that an upper portion of the sensor field of view is directed by said lens system at a downward angle through the container shoulder toward said light source, and a lower portion of the sensor field of view is directed by the lens system at an upward angle through the container heel toward the light source, and an information processor responsive to said sensor for detecting commercial variations in the container sidewall, shoulder and heel.

8. The apparatus set forth in claim 7 wherein said lens system includes a fresnel lens.

9. The apparatus set forth in claim 8 wherein said container positioning device includes means for rotating the container around an axis, and wherein said information processor scans said sensor at increments of container rotation.

10. The apparatus set forth in claim 9 wherein said positioning device is such that a front surface of the container is positioned adjacent to said lens system, and such that said lens system has a focal point disposed between said front surface and said light source.

11. The apparatus set forth in claim 7 wherein said lens system directs said field of view to a convergence point at said diffuse light source.

* * * * *